(12) United States Patent
Russell et al.

(10) Patent No.: US 11,484,728 B2
(45) Date of Patent: Nov. 1, 2022

(54) PHOTOTHERAPY FOR DOMESTICATED ANIMALS METHOD AND APPARATUS

(71) Applicants: Katharine Julia Russell, San Diego, CA (US); Stephen Douglas Russell, San Diego, CA (US)

(72) Inventors: Katharine Julia Russell, San Diego, CA (US); Stephen Douglas Russell, San Diego, CA (US)

(*) Notice: Subject to any disclaimer, the term of this patent is extended or adjusted under 35 U.S.C. 154(b) by 252 days.

(21) Appl. No.: 16/705,916

(22) Filed: Dec. 6, 2019

(65) Prior Publication Data

US 2021/0170191 A1 Jun. 10, 2021

(51) Int. Cl.
*A61N 5/06* (2006.01)
*A01K 29/00* (2006.01)
*A61N 5/067* (2006.01)

(52) U.S. Cl.
CPC ............ *A61N 5/06* (2013.01); *A01K 29/00* (2013.01); *A61N 5/067* (2021.08); *A61N 2005/0636* (2013.01); *A61N 2005/0645* (2013.01); *A61N 2005/0651* (2013.01); *A61N 2005/0654* (2013.01); *A61N 2005/0655* (2013.01); *A61N 2005/0663* (2013.01)

(58) Field of Classification Search
CPC .............. A61N 5/06; A61N 2005/0626; A61N 2005/0636; A61N 2005/0639; A61N 2005/0642; A61N 2005/0643; A61N 2005/065; A61N 2005/0661; A61N 2005/0662; A61N 2005/0663; A61N 2005/0665; A61N 2005/067

USPC .......... 607/88–91, 93–95; 128/898
See application file for complete search history.

(56) References Cited

U.S. PATENT DOCUMENTS

| | | | |
|---|---|---|---|
| 3,962,993 A * | 6/1976 | Dattilo | A01K 1/031 119/500 |
| 4,858,609 A * | 8/1989 | Cole | A61M 21/00 607/91 |
| 6,425,347 B1 * | 7/2002 | Bogner | A61D 3/00 119/315 |
| 6,427,631 B1 | 8/2002 | Ross | |
| 6,553,940 B1 | 4/2003 | Powell et al. | |
| D545,507 S | 6/2007 | Harper et al. | |
| 7,934,472 B2 * | 5/2011 | Weatherford | A01K 1/033 119/448 |
| 9,107,385 B2 | 8/2015 | Lever | |
| 10,413,746 B1 | 9/2019 | Pryor et al. | |
| 2008/0125620 A1 * | 5/2008 | McNew | A61M 21/02 600/27 |

(Continued)

OTHER PUBLICATIONS

S. Sivaprasad et al., "Spare the rods and spoil the retina: revisted", Eye, 2016, pp. 189-192, vol. 30, Macmillan Publishers.

(Continued)

*Primary Examiner* — Ahmed M Farah

(57) ABSTRACT

A method and apparatus to provide phototherapy to companion animals. The apparatus includes at least one light source configured to flood illuminate inside a housing, a housing sized to surround at least one companion animal, and a control system to adjust the light flux and light duration of the at least one light source. The method includes providing said apparatus and flood illuminating at least one companion animal with a clinically significant light flux and light duration.

8 Claims, 5 Drawing Sheets

(56) References Cited

U.S. PATENT DOCUMENTS

| | | | | |
|---|---|---|---|---|
| 2010/0218435 | A1* | 9/2010 | Reeves | E04H 1/125 52/173.1 |
| 2011/0144725 | A1* | 6/2011 | Pryor | G16H 20/30 715/764 |
| 2011/0251657 | A1* | 10/2011 | Miyake | H05B 45/37 607/88 |
| 2012/0186524 | A1* | 7/2012 | Grajcar | A01K 45/00 119/6.8 |
| 2014/0107737 | A1* | 4/2014 | Murphy | A61M 21/00 607/90 |
| 2017/0080246 | A1* | 3/2017 | Knight | A61G 10/02 |
| 2017/0360011 | A1* | 12/2017 | Lakios | F21V 23/0457 |
| 2021/0275826 | A1* | 9/2021 | Kawarai | A61D 1/00 |

OTHER PUBLICATIONS

L. A. Sanassi, "Seasonal affective disorder: Is there light at the end of the tunnel?", Journal of the American Academy of PAs (JAAPA), Feb. 2014, pp. 18-22, vol. 27, No. 2, Li.

N. Hanford et al., "Light Therapy and Alzheimer's Disease and Related Dementia: Past, Present, and Future", Journal of Alzheimers Disease (J. Alzheimers Dis.), Jan. 1, 2013, pp.

F. Burkhart, "In The War On Opioids 525-nm LEDs Offer Hope", SPIE Professional, Oct.-Dec. 2019, pp. 30-33, SPIE.

D. S. Bradley, "Laser Therapy Today", American Veterinarian, Aug. 2018, pp. 1, 24-25, Intellisphere LLC.

* cited by examiner

PHOTOTHERAPY FOR DOMESTICATED ANIMALS METHOD AND APPARATUS

BACKGROUND OF THE INVENTION

The use of phototherapy (or light therapy) has long been established in the ultraviolet region of the spectrum for its healing effects and treatment of humans. Phototherapy has been used worldwide for nearly a century to treat chronic skin conditions such as psoriasis, vitiligo and severe eczema. In these cases, wavelengths in the ultraviolet region of the spectrum, typically about 280 nm to about 400 nm are used for localized illumination of the skin. Phototherapy which strikes the retina of human eyes with visible light is used to treat diabetic retinopathy, see for example S. Sivaprasad et al., "Spare the Rods and Spoil the Retina: Revisited," Eye, Vol. 30, 2016, pp. 189-192). Also, circadian rhythm disorders such as delayed sleep phase disorder, seasonal affective disorder, and also non-seasonal disorders in humans have employed phototherapy. See for example L. A. Sanassi, "Seasonal Effective Disorder: Is There Light at the End of the Tunnel," Journal of the American Academy of PAs (JAAPA), Vol. 27, No. 2, February 2014, pp. 18-22 and N. Hanford et al., "Light Therapy and Alzheimer's Disease and Related Dementia; Past, Present and Future," J. Alzheimers Dis., Vol. 33, No. 4, 1 Jan. 2013, pp. 913-922. Recently, applications of phototherapy is being explored to treat chronic pain in humans, see F. Burkhart, "In the War on Opioids 525-nm LEDs Offer Hope," SPIE Professional, October-December 2019, pp. 30-33.

Applications of phototherapy to domesticated animals is not, however, practiced in veterinary medicine in part due to having a suitable system and methods to employ. Traditional domestic animal kennels provide either a metallic cage structure or plastic enclosure with metallic caged openings and a metallic caged door. See for example T. A. Powell et al., "Dog Kennel," U.S. Pat. No. 6,553,940; M. Harper et al, "Pet Kennel," U.S. Pat. D545,507; A. G. Ross, "Pet Carrier," U.S. Pat. No. 6,427,631 and citations within. While suitable as a temporary housing of a small domestic animal, unfortunately they only provide for non-uniform illumination of natural light without any specific optical control through the cage openings. T. E. Lever et al., "Animal Kennel for Scientific Examination," U.S. Pat. No. 9,107,385 provides an animal kennel that is trapezoidal shaped to constrain the animal and is radiolucent for radiographic imaging and translucent for observation. This housing is for temporary housing during scientific examination, but would be inappropriate for phototherapy due to its physical constraints on the animal.

Intensive care unit (ICU) incubators, ICU cages and recovery boxes used in veterinary hospitals may contain radiative heating elements for forced air heating or incandescent heating lamps that provide infrared energy to warm an animal. They are designed for heating and cooling, and may also be configured to serve as an oxygen and/or as an anesthetic chamber. However, they do not provide light required for phototherapy.

There are a large number of housings used in the veterinary industry, examples commonly used are available from, for example, Snyder Manufacturing Company (http://snydermfg.com) to include individual and group cat housing, cat cottages, cage units, dog housing, dryer cages, kennel runs, birds/exotics and small animal housings. However, they do not provide light required for phototherapy.

B. Pryor et al., "Phototherapy Apparatus with Interactive User Interface," U.S. Pat. No. 10,413,746 and citations therein describe an interactive user interface for treating biological tissue of an animal or human target. This provides for ease of use for the practitioner to employ a treatment protocol, but teaches of a handheld wand with optical fiber input and does not disclose or make obvious the method and apparatus of the current invention.

Current laser therapy used for domesticated animals, see for example D. S. Bradley, "Laser Therapy Today," *American Veterinarian*, Vol. 3, No. 6, August 2018, pp. 1, 24-25, provide localized illumination using a handheld wand, and is not conducive to the broader application of phototherapy. Accordingly, there is a need for an apparatus and method to provide phototherapy for domesticated animals.

BRIEF SUMMARY OF THE INVENTION

This invention describes a method and apparatus to provide phototherapy to companion animals. The apparatus includes at least one light source configured to flood illuminate inside a housing, a housing sized to surround at least one companion animal, and a control system to adjust the light flux and light duration of the at least one light source. The method includes providing said apparatus and illuminating at least one companion animal with a clinically significant light flux and light duration. The embodiments of the method and apparatus discussed herein provide a housing for the companion animal or animals undergoing phototherapy treatment, and an exemplary method for application of phototherapy to companion animals. The embodiments of the method and apparatus discussed herein overcome the limitations of the prior art by providing a light source configured to flood illuminate inside a housing and an optically compatible housing for application of phototherapy to companion animals.

DETAILED DESCRIPTION OF THE INVENTION

This invention describes a method and apparatus to provide phototherapy to companion animals. The apparatus includes at least one light source configured to flood illuminate inside a housing, a housing sized to surround at least one companion animal, and a control system to adjust the light flux and light duration of the at least one light source.

The method includes providing said apparatus and illuminating at least one companion animal with a clinically significant light flux and light duration. The embodiments of the method and apparatus discussed herein provide a housing for the companion animal or animals undergoing phototherapy treatment, and an exemplary method for application of phototherapy to companion animals. The embodiments of the method and apparatus discussed herein overcome the limitations of the prior art by providing a light source configured to flood illuminate inside a housing and an optically compatible housing for application of phototherapy to companion animals.

Specifically, the embodiments discussed herein provide a method that may be beneficial for treatment or management of chronic pain, or other physiological or neurological conditions in companion animals. It is understood that different species of companion animals will require different phototherapy protocols, as such the teachings herein are representative of the phototherapy protocols to be provided, but must be tailored for the species and condition to be treated.

Further, in some embodiments, the apparatus is portable and may be relocated to a various places for treatment including a veterinary hospital, veterinary office, commercial building or home.

In some embodiments the illumination band is fixed, and in some embodiments the illumination band may be changed.

Additionally, some embodiments discussed herein allow for phototherapy treatment of one or more companion animals simultaneously.

Figure 1:
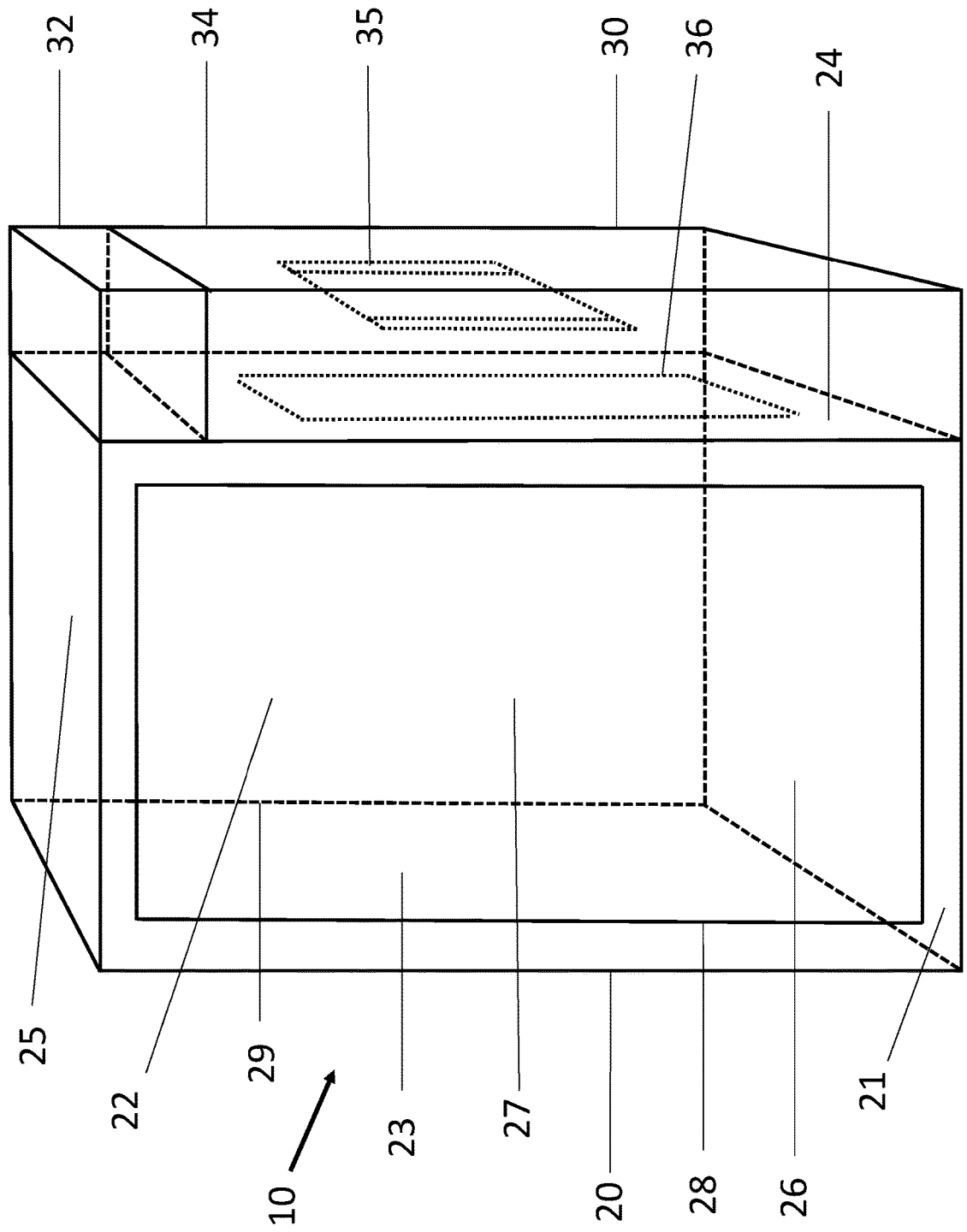
FIG. 1 shows a schematic view of an embodiment of an apparatus including a physical enclosure with optical coupling for phototherapy, in accordance with Phototherapy for Domesticated Animals Method and Apparatus.

FIG. 1 shows a schematic view of an embodiment of an apparatus including a physical enclosure with optical coupling for phototherapy, in accordance with Phototherapy for Domesticated Animals Method and Apparatus. Apparatus 10 includes a housing portion 20 and a controller portion 30 providing for the phototherapy protocols.

Housing portion 20 includes a front face 21, rear face 22, left face 23, right face 24, top face 25 and bottom face 26 that collectively define a cavity 27. Front face 21 includes an opening 28 to access cavity 27. Both left face 23 and right face 24 are equal in length, and front face 21 and rear face 22 are equal in length. The side faces 23 and 24 are generally not equal in length to the front 21 and rear 22 faces, but may be in some embodiments. For companion animals such as a rodent, rabbit and the like, side faces 23 and 24 may range from about 12 inches to about 18 inches in length, and front 21 and rear 22 faces may range from about 12 inches to about 18 inches in length and a height 29 from about 12 inches to about 18 inches.

For a small-sized companion animal such as a cat or small dog, side faces 23 and 24 may range from about 24 inches to about 36 inches in length, and front 21 and rear 22 faces may range from about 36 inches to about 42 inches in length and a height 29 from about 24 inches to about 30 inches. For a medium-sized companion animal such as medium-sized dog, side faces 23 and 24 may range from about 24 inches to about 36 inches in length, and front 21 and rear 22 faces may range from about 48 inches to about 72 inches in length and a height 29 from about 36 inches to about 42 inches. For a larger companion animal such as a large dog, side faces 23 and 24 may range from about 72 inches to about 84 inches in length and front 21 and rear 22 faces may range from about 36 inches to about 42 inches in length and a height 29 from about 72 inches to about 84 inches. Front face 21 may also contain a door, not shown, to cover, substantially cover or at least partially cover opening 28. The door may be affixed to front face 21 via hinges, rails, and the like as common practice. The door may be transparent, translucent, or a standard grating as desired. Housing portion 20 is configured to be operably coupled to controller portion 30. The height 29 of housing portion 20 is sufficient to create cavity 27 which encloses the patient but may be larger if desired for the job at hand. Housing portion 20 may be fabricated in a variety of sizes to accommodate companion animals of different sizes.

The housing portion 20 described herein is not usually designed for prolonged lengths of stay, and generally would be used for durations of less than one week for phototherapy treatment in accordance with this invention. While the above dimensions are exemplary, in the preferred embodiment the enclosures should provide sufficient space to allow each animal, regardless of species, to make normal postural adjustments, e.g., to turn freely and to easily stand, sit, stretch, move their head, without touching the top of the enclosure, lie in a comfortable position with limbs extended, move about and assume a comfortable posture for feeding, drinking, urinating and defecating. In addition, cats and dogs should be able to hold their tails erect when in a normal standing position. The enclosures should allow animals to see out but should also provide at least some opportunity to avoid visual contact with other animals.

Controller portion 30 is comprised of a user interface module 32 and a functional module 34. Functional module 34 includes a light source 35 that may be an incandescent light, a fluorescent light, a laser, a light-emitting diode (LED) or an array of light sources configured to provide the desired wavelength and flux for the phototherapy protocol. Light source 35 may be a continuous wave or pulse wave source, and may have a single wavelength, multiple wavelengths, or operate over one wavelength bands. Light source 35 may also include fixed or variable optical elements including filters, lenses, mirrors, waveguides, diffusers and/or attenuators operably connected to provide the desired wavelength or wavelength band and flux for the phototherapy protocol. Accordingly, the fixed or variable optical elements including filters, lenses, mirrors, waveguides, diffusers and/or attenuators may be physically attached to apparatus 10. Typically, light source 35 operates in the wavelength range of about 380 nm to about 750 nm. Light source 35 is operably coupled through aperture 36 to cavity 27 to provide a flood illumination at the desired wavelength band and flux for the phototherapy protocol. Light source 35 and associated optical elements may provide illumination in the violet (about 380 nm to about 450 nm), blue (about 450 nm to about 495 nm), green (about 495 nm to about 570 nm), yellow (about 570 nm to about 590 nm), orange (about 590 nm to about 620 nm) or red (about 620 nm to about 750 nm) bands. Light source 35 and associated optical elements may provide illumination characteristic of the solar spectrum (about 380 nm to about 780 nm) with illuminance of about 50 lux to about 100,000 lux or lunar spectrum (about 380 nm to about 780 nm) with illuminance of about 0.01 lux to about 1 lux. Light source 35 and associated optical elements may provide illumination that can be switched between multiple bands.

Functional module 34 further includes control electronics as in common practice to provide power to light source 35 and user interface module 32. Controller portion 30 may be configured to be operably connected to housing portion 20 from alternative faces if desired.

In some embodiments, at least some of the inner portions of the sides 21, 22, 23, 24, 25 and 26 forming cavity 27 are made reflective to the desired wavelength band of the phototherapy. In some embodiments, the reflective inner portions of the sides may be specular or diffusive reflection for the job at hand. In some embodiments, the housing portion 20 is comprised of a material that is easily cleaned or sterilized between patients, and may be fabricated out of stainless steel, polycarbonate, fluoropolymers, materials with non-porous surfaces and the like. In some embodiments, housing portion 20 may also be configured to provide heating or cooling to cavity 27, and/or to provide a desired atmospheric environment such as increased oxygen concentration. In some embodiments, housing portion 20 may also be configured to include, for example, a pet mat or pet bed or preferably a "vet pad" or "vet fleece" which is a unique blend of fiber that is both thick and dense. The fiber of a "vet pad" or "vet fleece" whisks moisture away while providing soft, stable and comfortable liner and bedding as practiced in the art of veterinary medicine. The fiber is non-allergenic, non-toxic, non-irritant, will not support bacterial growth and is machine washable, bleachable and dryable. In some embodiments, apparatus 10 may also be configured with components to provide food, water, warming blankets (e.g. Bair Huggers™), medications and waste management as called for in the field of veterinary medicine for the specific treatment protocol. In some embodiments, housing portion 20 of apparatus 10 is at least partially open on one or more sides to maximize ventilation. While there are many size variations possible with apparatus 10, housing portion 20 and controller portion 30 are sized so they may be operably configured together.

As an example, user interface module 32 is typically comprised of at least a power switch and means to set the desired flux and illumination duration for the phototherapy. User interface module 32 may also include a means to change the wavelength band of the illumination if the functional module 34 is designed with that functionality. User interface module 32 may employ a user configured interface similarly to that described in U.S. Pat. No. 10,413, 746, to Pryor et al., the content of which is fully incorporated by reference herein.

In some embodiments, controller portion 30 may be configured to operably couple to one or more housing portions 20. In some embodiments, user interface module 32 may be configured to interface with one or more light sources 35.

In some embodiments, apparatus 10 may also be configured with wheels for ease in transporting or for attachments to concatenate multiple units together to treat multiple domesticated animals simultaneously. In some embodiments, apparatus 10 may be configured on a stand, pedestal or storage unit to provide for a desired working height above the floor. In some embodiments, apparatus 10 may be physically attached to another structure.

Figure 2:
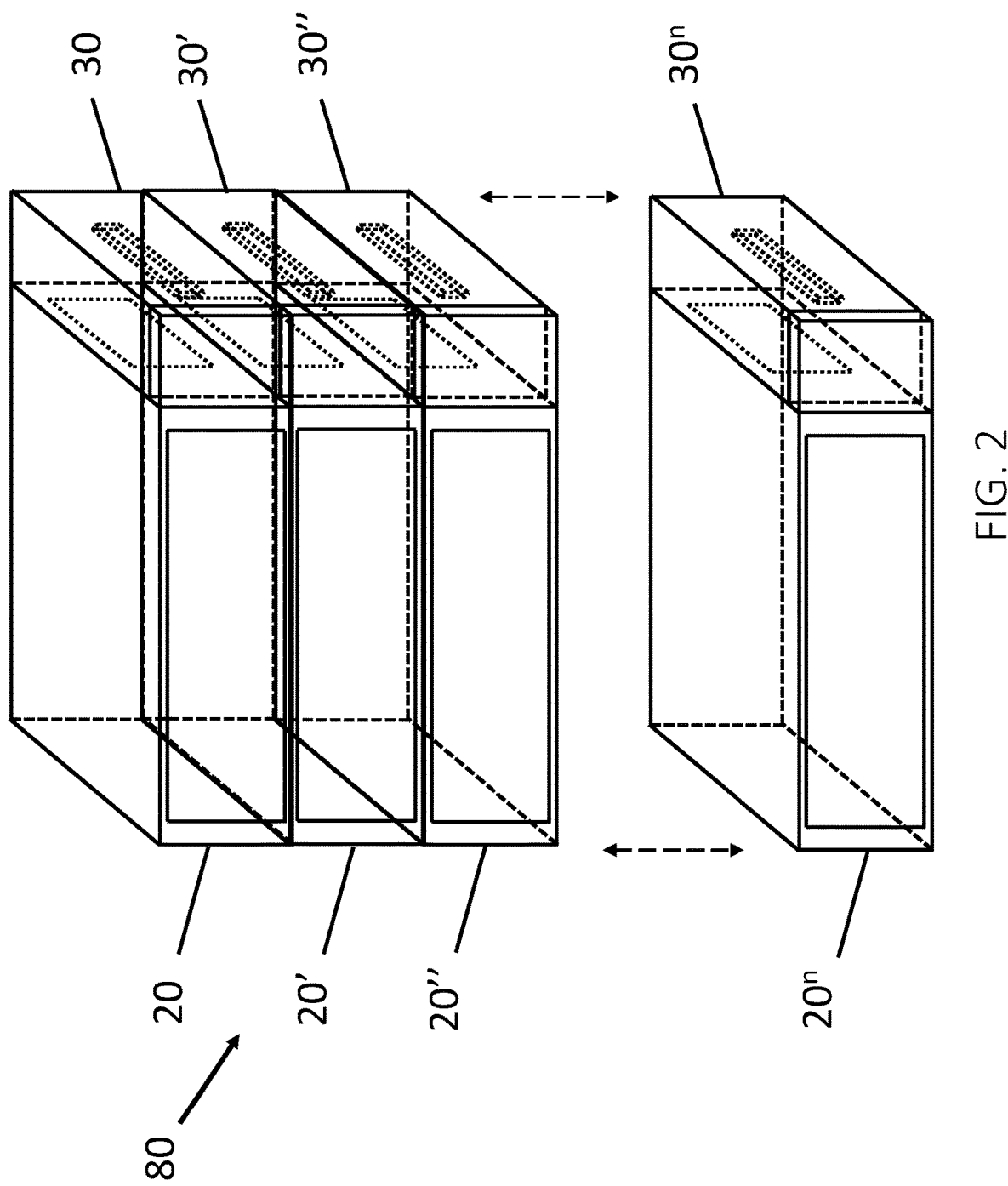
FIG. 2 shows a schematic view of an embodiment of an apparatus including a plurality of physical enclosures with optical coupling for phototherapy, in accordance with Phototherapy for Domesticated Animals Method and Apparatus.

FIG. 2 shows a schematic view of an embodiment of an apparatus including a plurality of physical enclosures with optical coupling for phototherapy, in accordance with Phototherapy for Domesticated Animals Method and Apparatus. Apparatus 80 includes a housing portion 20 and a controller portion 30 providing for the phototherapy protocols as described in FIG. 1. Apparatus 80 further includes additional housing portions 20', 20", ... 20" and controller portions 30', 30", ... 30" where the n+1 portions are functionally concatenated into a single apparatus 80. In this embodiment, the number housing portions and controller portions are both equal to n+1, however in some embodiments the number of housing portions and controller portions may not be equal. For example, apparatus 80 may be configured so that one controller portion 30 can provide the phototherapy protocols of a plurality of housing portions.

Figure 3:
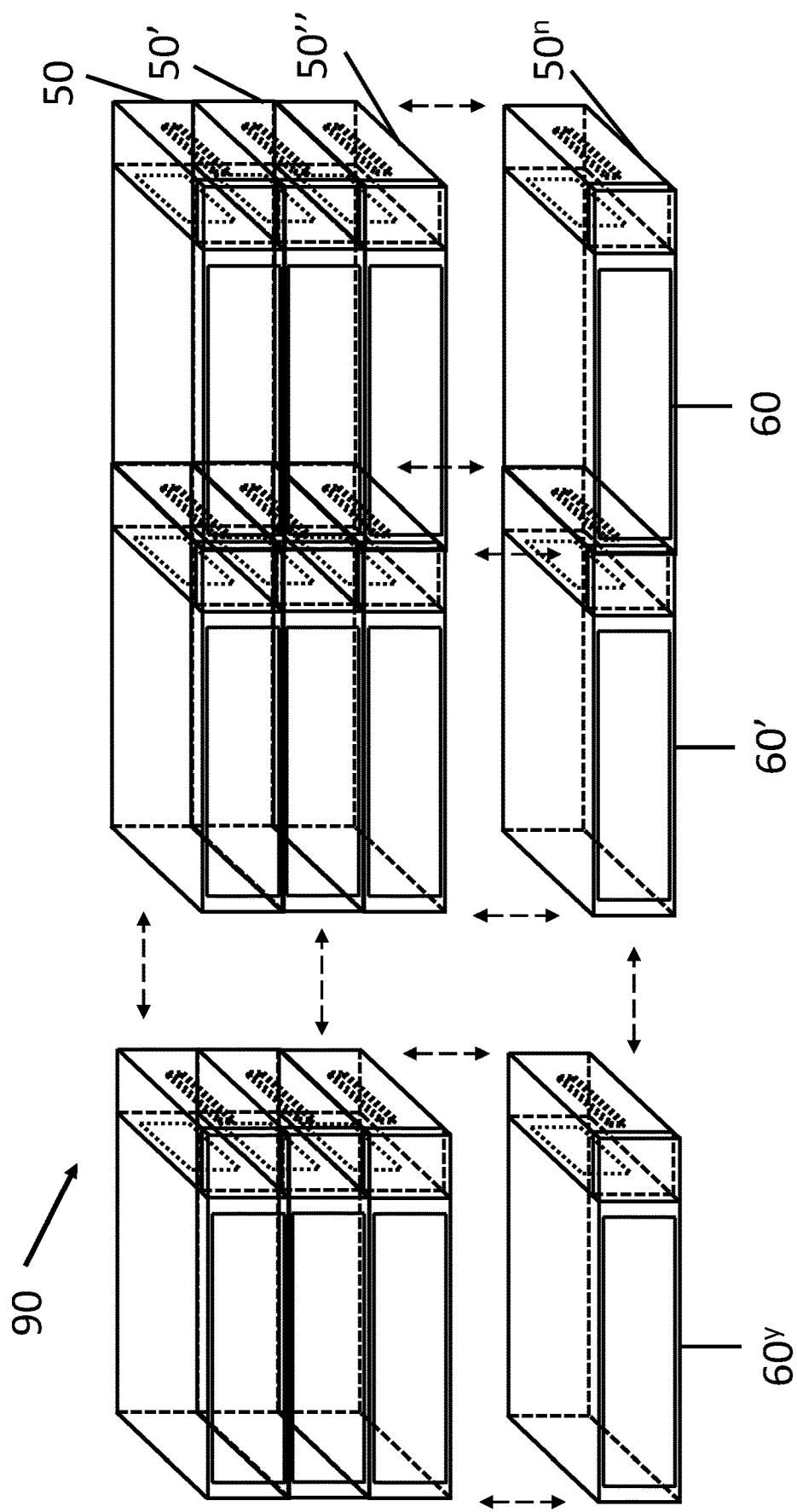
FIG. 3 shows a schematic view of an embodiment of an apparatus including a plurality of physical enclosures in an array with optical coupling for phototherapy, in accordance with Phototherapy for Domesticated Animals Method and Apparatus.

FIG. 3 shows a schematic view of an embodiment of an apparatus including a plurality of physical enclosures in an array with optical coupling for phototherapy, in accordance with Phototherapy for Domesticated Animals Method and Apparatus.

Apparatus 90 includes a vertical apparatus portion 50 in accordance with apparatus 10 in FIG. 1 including a housing portion 20 and a controller portion 30 providing for the phototherapy protocols as shown in FIG. 1 as described above. Apparatus 90 further includes additional vertical apparatus portions 50', 50", ... 50" in a vertical configuration as described by Apparatus 80 in FIG. 2 and a horizontal apparatus portion 60 in accordance with apparatus 10 in FIG. 1 and additional horizontal apparatus portions 60', ... 60$^y$ in a horizontal configuration where the vertical nil portions and the horizontal y+1 portions are functionally concatenated into a single apparatus 90. In typically configurations, due to physical space considerations, n and y are each less than 10. In this embodiment, the number of vertical portions n+1 and the number of horizontal portions y+1 are not equal, however in some embodiments the number may be equal.

Figure 4:
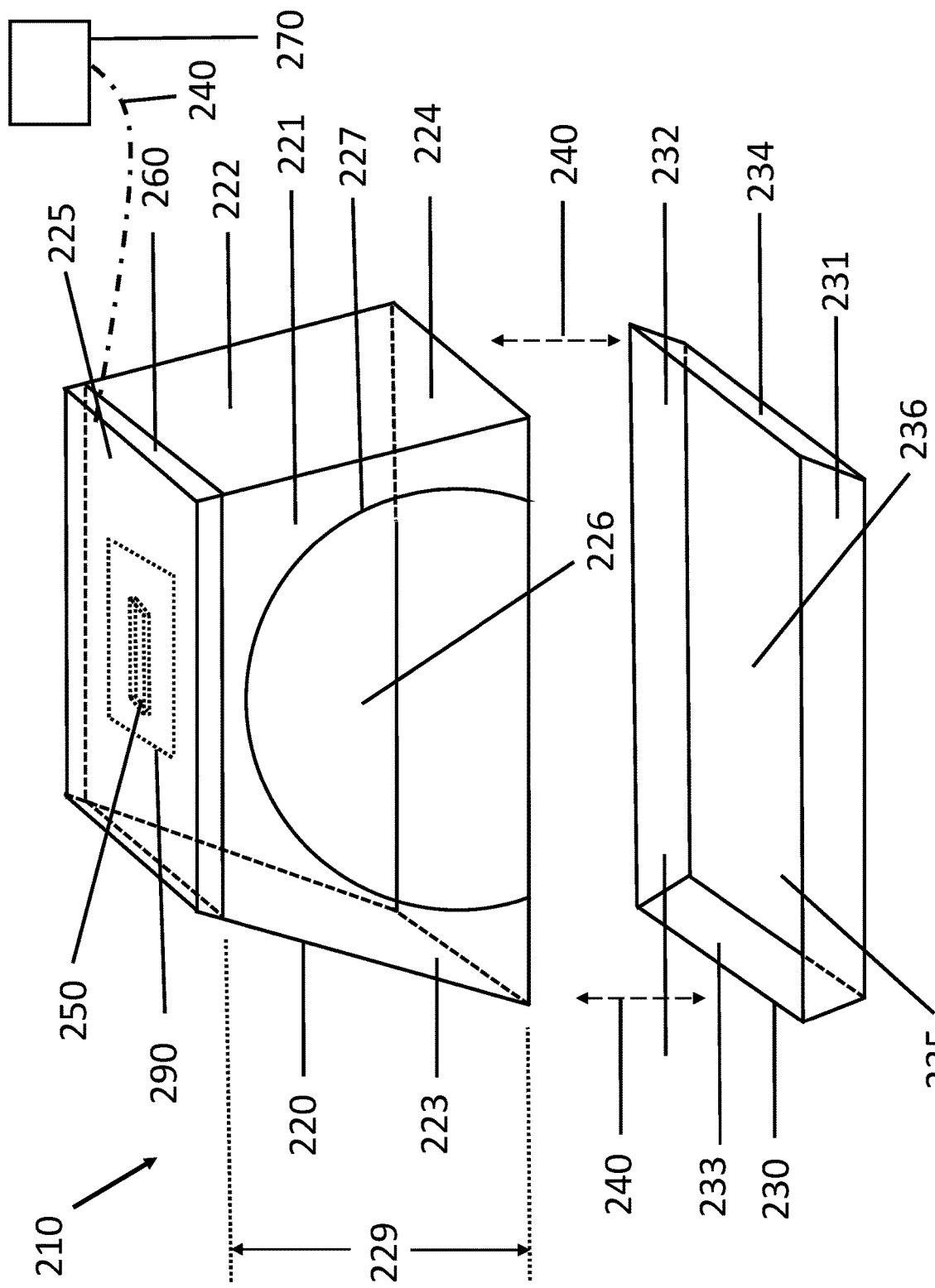
FIG. 4 shows a schematic view of an embodiment of an apparatus including a portable physical enclosure with optical coupling for phototherapy, in accordance with Phototherapy for Domesticated Animals Method and Apparatus.

FIG. 4 shows a schematic view of an embodiment of an apparatus including a physical enclosure with optical coupling for phototherapy, in accordance with Phototherapy for Domesticated Animals Method and Apparatus. Apparatus 210 includes a top portion 220, a bottom portion 230, and a means 240 to attach and de-attach top portion 220 from bottom portion 230, light source 250 and control system 260 for operating the phototherapy protocols.

Top portion 220 includes a front face 221, rear face 222, left face 223, right face 224 and top face 225 that collectively define an open cavity 226 whose top view may be approximately square, approximately rectangular or approximately trapezoidal. In other words, the faces need not be aligned at right angles to the bottom face or each other. Both left face 223 and right face 224 are equal in length, and front face 221 and rear face 222 are equal in length. The side faces 223 and 224 are generally not equal in length to the front 221 and rear 222 faces, but may be in some embodiments. For companion animals such as a rodent, rabbit and the like, side faces 223 and 224 may range from about 12 inches to about 18 inches in length, and front 221 and rear 222 faces may range from about 12 inches to about 18 inches in length and a height 229 from about 12 inches to about 18 inches.

For a small-sized companion animal such as a cat or small dog, side faces 23 and 24 may range from about 24 inches to about 36 inches in length, and front 21 and rear 22 faces may range from about 36 inches to about 42 inches in length and a height 229 from about 24 inches to about 30 inches. For a medium-sized companion animal such as medium-sized dog, side faces 223 and 224 may range from about 24 inches to about 36 inches in length, and front 221 and rear 222 faces may range from about 48 inches to about 72 inches in length and a height 229 from about 36 inches to about 42 inches. For a larger companion animal such as a large dog, side faces 223 and 224 may range from about 72 inches to about 84 inches in length and front 221 and rear 222 faces may range from about 36 inches to about 42 inches in length and a height 229 from about 72 inches to about 84 inches. The bottom edges of faces 221, 222, 223 and 224 which define the lowermost extent of cavity 226 may contain a flange or other alignment means, not shown, for aligning top portion 220 to bottom portion 230 for assembly. Front face 221 contains a cutout region 227 for access to open cavity 226. Cutout region 227 may be a uniform or irregular shape sized sufficiently to access open cavity 226. Front face 221 may also contain a door, not shown, to cover, substantially cover or at least partially cover cutout region 227. The door may be affixed to top portion 220 via hinges, rails, and the like as common practice. The door may be transparent, translucent, or a standard grating as desired. The top portion 220 is comprised of a material that contains at least one portion 290 that is at least partially transparent to the wavelength of light to be applied for phototherapy treatment. Top portion 220 is configured to include at least one light source operably 250 coupled to flood illuminate open cavity 226. The height 229 of top portion 220 is sufficient to create cavity 226 which encloses the patient but may be larger if desired for the job at hand. Top portion 220 may be fabricated in a variety of sizes to accommodate animals of different sizes.

The apparatus 210 described herein is not designed for prolonged lengths of stay, and generally would be used for durations of less than one week for phototherapy treatment in accordance with this invention. While the above dimensions are exemplary, in the preferred embodiment the enclosures should provide sufficient space to allow each animal, regardless of species, to make normal postural adjustments, e.g., to turn freely and to easily stand, sit, stretch, move their head, without touching the top of the enclosure, lie in a comfortable position with limbs extended, move about and assume a comfortable posture for feeding, drinking, urinating and defecating. In addition, cats and dogs should be able to hold their tails erect when in a normal standing position. The enclosures should allow animals to see out but should also provide at least some opportunity to avoid visual contact with other animals.

Light source 250 may be an incandescent light, a fluorescent light, a laser, a light-emitting diode (LED) or array of light sources configured to provide the desired wavelength and flux for the phototherapy protocol. Light source 250 may be a continuous wave or pulse wave source. Light source 250 may also include fixed or variable fixed or variable optical elements including filters, lenses, mirrors, waveguides, diffusers and/or attenuators operably connected to provide a flood illumination at the desired wavelength band and flux for the phototherapy protocol. Accordingly, the fixed or variable optical elements including filters, lenses, mirrors, waveguides, diffusers and/or attenuators may be physically attached to apparatus 210 on at least part of upper portion 220. Typically, light source 250 operates in the wavelength range of about 400 nm to 700 nm. Light source 250 and associated optical elements may provide illumination in the violet (about 380 nm to about 450 nm), blue (about 450 nm to about 495 nm), green (about 495 nm to about 570 nm), yellow (about 570 nm to about 590 nm), orange (about 590 nm to about 620 nm) or red (about 620 nm to about 750 nm) bands. Light source 250 and associated optical elements may provide illumination characteristic of the solar spectrum (about 380 nm to about 780 nm) with illuminance of about 50 lux to about 100,000 lux or lunar spectrum (about 380 nm to about 780 nm) with illuminance of about 0.01 lux to about 1 lux. Light source 250 and associated optical elements may provide illumination that can be switched between multiple bands.

Bottom portion 230 includes a front face 231, rear face 232, left face 233, right face 234 and bottom 235 that collectively define an open cavity 236 whose top view may be approximately square, approximately rectangular or approximately trapezoidal. In other words, the faces need not be aligned at right angles to the bottom face or each other. Both left face 233 and right face 234 are equal in length, and front face 231 and rear face 232 are equal in length. The side faces 233 and 234 are generally not equal in length to the front 231 and rear 232 faces, but may be in some embodiments. Bottom portion 230 is sized to operably connect to top portion 220 for the size of the companion animal undergoing treatment. The top edges of faces 231, 232, 233 and 234 which define the uppermost extent of cavity 236 may contain a grooved flange or other alignment means, not shown, for aligning top portion 220 to bottom portion 230 for assembly. In some embodiments, front face 231 may also contain a cutout region, not shown, for easier access to open cavity 226 and cavity 236. The bottom portion 230 is comprised of a material that is easily cleaned, and in some embodiments preferably autoclaved or sterilized between patients, and may be fabricated out of stainless steel, polycarbonate, fluoropolymers, non-porous material and the like. Bottom portion 230 may also be configured to include, for example, a pet mat or pet bed or preferably a "vet pad" or "vet fleece" which is a unique blend of fiber that is both thick and dense. The fiber of a "vet pad" or "vet fleece" whisks moisture away while providing soft, stable and comfortable liner and bedding as practiced in the art of veterinary medicine. The fiber is non-allergenic, non-toxic, non-irritant, will not support bacterial growth and is machine washable, bleachable and dryable. The height of bottom portion 230 is sufficient to enclose the desired mat or pad describe above, and typically ranges from about 1 inch to about 6 inches, but may be larger if desired for the job at hand. Bottom portion 230 may be fabricated in a variety of sizes to accommodate animals of different sizes. While there are many size variations possible with apparatus 210, top portion 220 and bottom portion 230 are sized so they may be operably configured together. Bottom portion 230 may also be configured with wheels for ease in transporting or for attachments to concatenate multiple units together to treat multiple animals simultaneously. Bottom portion 230 may also be configured on a stand, pedestal or storage unit to provide for a desired working height above the floor. In some embodiments, apparatus 210 may be physically attached to another structure. In some embodiments, bottom portion 230 of apparatus 210 may also be configured with components to provide food, water, warming blankets (e.g. Bair Huggers™), medications and waste management as called for in the field of veterinary medicine for the specific treatment protocol. In some embodiments, top portion 220 of apparatus 210 is at least partially open to maximize ventilation.

Controller system 260 includes a light source 250 that may be an incandescent light, a fluorescent light, a laser, a light-emitting diode (LED) or an array of light sources configured to provide flood illumination at the desired wavelength band and flux for the phototherapy protocol. Light source 250 may be a continuous wave or pulse wave source, and may have a single wavelength, multiple wavelengths, or operate over one wavelength bands. Light source 250 may also include fixed or variable optical elements including filters, lenses, mirrors, waveguides, diffusers and/or attenuators operably connected to provide flood illumination at the desired wavelength or wavelength band and flux for the phototherapy protocol. Accordingly, the fixed or variable optical elements including filters, lenses, mirrors, waveguides, diffusers and/or attenuators may be physically attached to apparatus 210. Accordingly, the fixed or variable optical filters may be physically attached to at least part of apparatus 210, for example over aperture 290 to act on the light emitted from light source 250. Typically, light source 250 operates in the wavelength range of about 380 nm to about 750 am. Light source 250 is operably coupled through aperture 290 to cavity 226 and 236 to provide the desired wavelength and flux for the phototherapy protocol. Light source 250 and associated optical elements may provide illumination in the violet (about 380 nm to about 450 nm), blue (about 450 nm to about 495 nm), green (about 495 nm to about 570 nm), yellow (about 570 nm to about 590 nm), orange (about 590 nm to about 620 nm) or red (about 620 nm to about 750 nm) bands. Light source 35 and associated optical elements may provide illumination characteristic of the solar spectrum (about 380 nm to about 780 nm) with illuminance of about 50 lux to about 100,000 lux or lunar spectrum (about 380 nm to about 780 nm) with illuminance of about 0.01 lux to about 1 lux. Light source 250 and associated optical elements may provide illumination that can be switched between multiple bands.

Apparatus 210 further includes control electronics in control system 260 as in common practice to provide power to light source 250 and user interface module 270. User interface module 270 is operably coupled 240 to control system 260. The means to operably couple may include through an electrically conductive cable, and optical fiber or wirelessly by electromagnetic radiation, for example Bluetooth, WiFi™ (i.e. conforms to IEEE 802.11x standard) or LiFi (i.e. Light Fidelity or visible light communications). Control system 260 may be configured to be operably connected to top portion 220 from multiple or alternative faces if desired.

As an example, control system 260 may employ a user interface module 270 configured similarly to that described in U.S. Pat. No. 10,413,746, to Pryor et al., the content of which is fully incorporated by reference herein. Many modifications and variations of the Phototherapy for Domesticated Animals Method and Apparatus are possible in light of the above description. Within the scope of the appended claims, the Phototherapy for Domesticated Animals Method and Apparatus may be practiced otherwise than as specifically described. The scope of the claims is not limited to the implementations and embodiments disclosed herein, but extends to other implementations and embodiments as may be contemplated by those having ordinary skill in the art.

Figure 5:
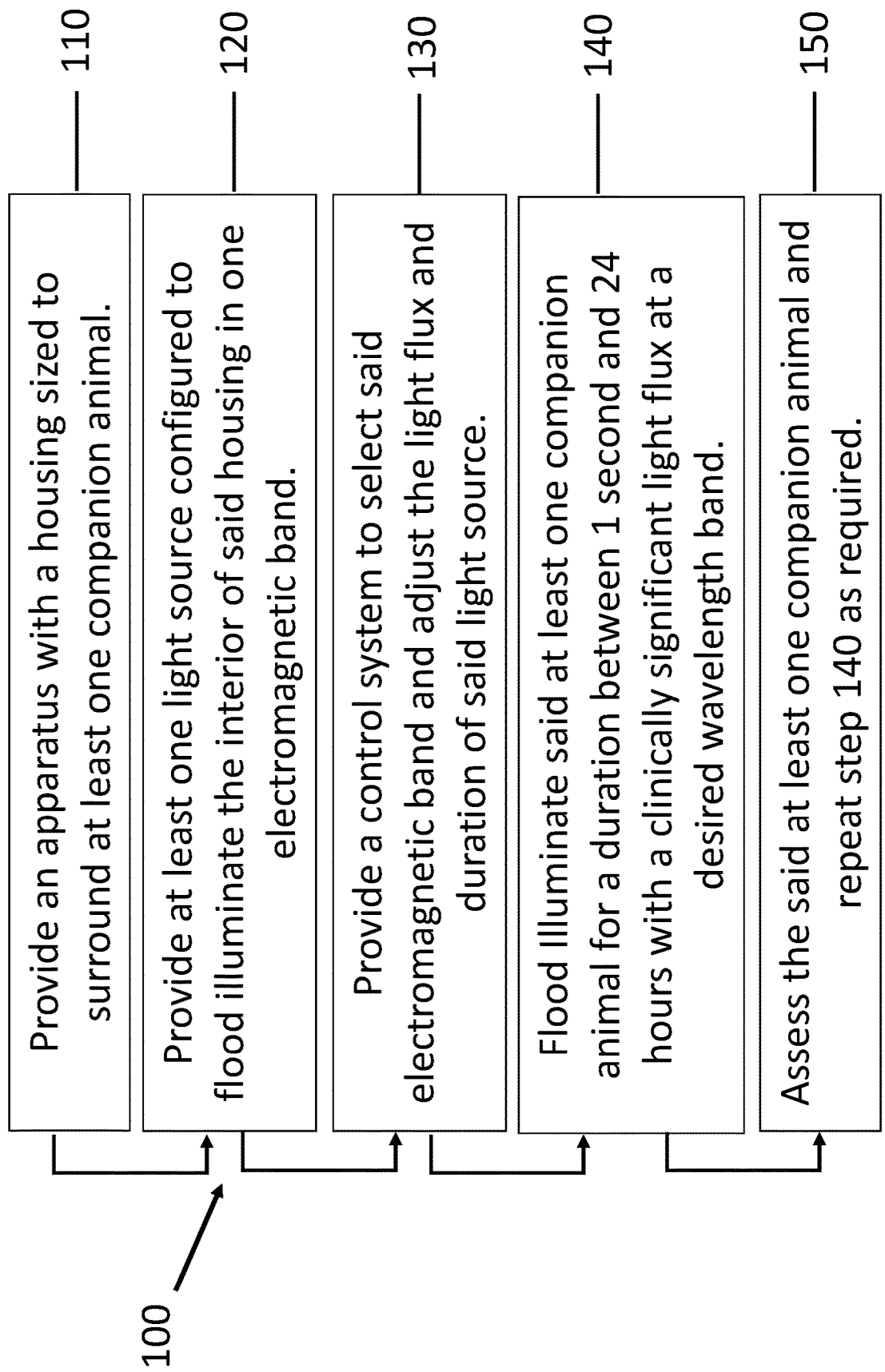
FIG. 5 shows a flowchart of an embodiment of a method for phototherapy in accordance with Phototherapy for Domesticated Animals Method and Apparatus.

FIG. 5 shows a flowchart of an embodiment of a method for phototherapy in accordance with Phototherapy for Domesticated Animals Method and Apparatus. Specifically, FIG. 5 shows a flowchart of an embodiment of a method 100 for phototherapy in accordance with Phototherapy for Domesticated Animals Method and Apparatus. Method 100 begins at step 110, providing an apparatus with a housing sized to surround at least one companion animal. In some embodiments, the housing may be apparatus 10 in FIG. 1, apparatus 80 in FIG. 2, apparatus 90 in FIG. 3, apparatus 210 in FIG. 4, or other modifications by those of ordinary skill in the art based on the teachings disclosed herein.

Step 120 provides at least one light source and associated optical elements configured to flood illuminate the interior of the housing in one spectral or electromagnetic band on the companion animal or animals undergoing phototherapy treatment. In some embodiments, the wavelength of the light source may be variable to accommodate different phototherapy protocols as required for treatment. In the preferred embodiment, wavelengths may extend from about 380 nm to about 750 nm, but may be either broadband across the visible spectrum or narrow-band as called for in the medical protocol. The method 100 may provide illumination in the violet (about 380 nm to about 450 nm), blue (about 450 nm to about 495 nm), green (about 495 nm to about 570 nm), yellow (about 570 nm to about 590 nm), orange (about 590 nm to about 620 nm) or red (about 620 nm to about 750 nm) bands. The method 100 may provide illumination characteristic of the solar spectrum (about 380 nm to about 780 nm) with illuminance of about 50 lux to about 100,000 lux or lunar spectrum (about 380 nm to about 780 nm) with illuminance of about 0.01 lux to about 1 lux.

The next step 130 is to provide a control system such as controller system 30 in FIG. 1, controller systems 30, 30', 30", . . . 30" in FIG. 2, controller system 50, 50', 50", . . . , 50" in FIG. 3, controller system 260 in FIG. 4, or other modifications by those of ordinary skill in the art based on the teachings disclosed herein to set the desired treatment protocol. Treatment protocols may require setting the illumination wavelength band, lux, and duration for the job at hand, and may depend on species, age, and weight as established by the veterinary medical community for the phototherapy protocol desired. Typically lux will range from about 0.001 lux to a maximum of about 100,000 lux depending on the optical response of the companion animal under treatment and medical protocol required, where 1 lux=1 lumen/rm.

Step 140 is flood illuminating at least one companion animal for a duration between 1 second and 24 hours with a clinically significant light flux at the desired wavelength band.

Step 150 includes assessing the at least one companion animal under treatment and repeat Step 140 as required.

Many modifications and variations of the Phototherapy for Domesticated Animals Method and Apparatus are possible in light of the above description. It is understood that different species of companion animals will require different phototherapy protocols to exhibit clinically significant results, as such the teachings herein are representative of the phototherapy protocols to be provided, but must be tailored for the species and condition to be treated. Within the scope of the appended claims, the Phototherapy for Domesticated Animals Method and Apparatus may be practiced otherwise than as specifically described. The scope of the claims is not limited to the implementations and embodiments disclosed herein, but extends to other implementations and embodiments as may be contemplated by those having ordinary skill in the art.

We claim:

1. An apparatus to provide phototherapy to companion animals comprising:
   at least one light source configured to flood illuminate the inside of a housing in one wavelength band selected from violet, blue, green, yellow, orange, or red; a housing sized to surround at least one companion animal; and
   a control system to adjust the light flux and light duration of said at least one light source, wherein specifically tailored phototherapy protocols are provided for the species and conditions to be treated, thereby providing clinically significant results.

2. The apparatus of claim 1, wherein the said housing comprises a portable housing.

3. The apparatus of claim 1, wherein said housing includes attachments to concatenate multiple units together to treat multiple companion animals simultaneously.

4. The apparatus of claim 1, wherein said light flux is between 0.01 lux and 100,000 lux and said light duration is between 1 second and 24 hours is clinically significant.

5. The apparatus of claim 1, wherein the light flux is between 0.01 lux and 100,000 lux.

6. A method to provide phototherapy to companion animals comprising the steps of:
- providing a housing sized to surround at least one companion animal;
- providing at least one light source configured to flood illuminate the inside of said housing in one wavelength band selected from violet, blue, green, yellow, orange, or red;
- providing a control system to adjust the light flux and light duration of said at least one light source on said at least one companion animal; and
- flood illuminating said at least one companion animal for a duration between 1 second and 24 hours with a clinically significant light flux between 0.01 lux and 100,000 lux.

7. A method of claim 6, where said illuminating is repeated at least once per day.

8. A method of claim 6, wherein said domesticated animals include exotics, companion and farm animals.

* * * * *